United States Patent
Riemenschneider et al.

(10) Patent No.: US 8,521,263 B2
(45) Date of Patent: Aug. 27, 2013

(54) METHOD AND DEVICE FOR RECORDING AN ELECTROCARDIOGRAM

(75) Inventors: Markus Riemenschneider, Taunusstein (DE); Klaus Bonaventura, Berlin (DE); Felix Brand, Frankfurt am Main (DE)

(73) Assignee: Personal Medsystems GmbH, Berlin (DE)

( * ) Notice: Subject to any disclaimer, the term of this patent is extended or adjusted under 35 U.S.C. 154(b) by 0 days.

(21) Appl. No.: 13/255,895

(22) PCT Filed: Jan. 25, 2010

(86) PCT No.: PCT/EP2010/000417
§ 371 (c)(1),
(2), (4) Date: Sep. 9, 2011

(87) PCT Pub. No.: WO2010/102695
PCT Pub. Date: Sep. 16, 2010

(65) Prior Publication Data
US 2011/0319781 A1      Dec. 29, 2011

(30) Foreign Application Priority Data
Mar. 9, 2009    (DE) .......................... 10 2009 012 352

(51) Int. Cl.
*A61B 5/0402*       (2006.01)
(52) U.S. Cl.
USPC ......................................... 600/509; 600/508
(58) Field of Classification Search
USPC ....................................................... 600/508
See application file for complete search history.

(56) References Cited

U.S. PATENT DOCUMENTS

| | | | |
|---|---|---|---|
| 7,860,558 B2 * | 12/2010 | Feild et al. | 600/509 |
| 2007/0129639 A1 * | 6/2007 | Zhang et al. | 600/509 |
| 2007/0232946 A1 | 10/2007 | Feild et al. | |

FOREIGN PATENT DOCUMENTS

EP   0 712 605 A1   5/1996

OTHER PUBLICATIONS

International Search Report for application PCT/EP2010/000417 filed on Jan. 25, 2010.
Written Opinion of International Searching Authority for application PCT/EP2010/000417 filed on Jan. 25, 2010.
Jan A. Kors et al., "Accurate Automatic Detection of Electrode Interchange in the Electrocardiogram", The American Journal of Cardiology, Aug. 15, 2001, pp. 396-399, vol. 88 No. 4, Excerpta Medica, Inc.
G. Bázs et al., "Intelligent Cardiac Telemonitoring System", Computers in Cardiology. 2004, pp. 745-748, vol. 31, IEEE.

* cited by examiner

*Primary Examiner* — Carl H Layno
*Assistant Examiner* — Paula J Stice

(57) ABSTRACT

The invention relates to a method for recording an electrocardiogram, for example, comprising the steps of: a) receiving electrocardiogram signals from at least two electrodes (2, 3, 4, 5); b) calculating a current electrocardiogram from the received electrocardiogram signals, assuming an arrangement of the electrodes (2, 3, 4, 5); c) determining a deviation of the calculated current electrocardiogram from a reference electrocardiogram; d) repeating the steps b) and c), wherein each repetition assumes a different electrode arrangement; and e) identifying which of the determined deviations is the minimum.

15 Claims, 5 Drawing Sheets

METHOD AND DEVICE FOR RECORDING AN ELECTROCARDIOGRAM

FIELD OF THE INVENTION

The present invention relates generally to a method and a device for measuring electrical heart signals and particularly to a method and a device for recording an electrocardiogram.

BACKGROUND OF THE INVENTION

General devices and methods for measuring the electrical activities of the heart of living beings, particularly of humans, are known.

For measuring the heart activity so-called electrocardiographs are known which measure electrical potentials in the heart muscle on the skin surface by using single electrodes attached to the subject to be examined.

The electrodes can be attached to or placed on points of the body in various configurations in order to measure, i.e., derive the respective potentials at each point. Various lead systems exist, using not only varying numbers of electrodes but also varying points on the body to derive each individual signal. The potentials are generally measured between two specified electrodes. The measured potential in time forms the so-called electrocardiogram.

In principle a physician or an automatic analyzing algorithm needs to know the arrangement of the electrodes, and between which electrodes the individual potentials are measured in order to be able to interpret an electrocardiogram in a meaningful way.

As shown, for example, in prior art DE 100 65 578 A1 it frequently occurs in practice that the electrodes are not attached exactly in the position specified for the lead system, and that, in addition, the electrodes are interchanged. The method disclosed there uses a lead system working with 10 electrodes, and is able to recognize interchanged or incorrectly positioned electrodes by means of a vector analysis or vectorcardiography. This vector analysis is based on assigning a vector to each electrode and comparing the result of the vector analysis with a reference result. In case of an adequate deviation the system recognizes that electrodes have been interchanged.

Furthermore, conversion of different lead systems to each other is known, using, for example, vectorcardiography. For example, U.S. Pat. No. 4,850,370 discloses a lead system using only 4 electrodes to convert into a 10- or 12-channel electrocardiogram.

As mentioned above, placing of the electrodes and, in particular, the correct assignment, i.e. the correct "permutation" of electrodes are prone to errors. Even trained personnel frequently chose an incorrect electrode permutation, even when electrodes and associated signal inputs of an electrocardiograph are color coded.

Due to an increasing number of cardiovascular diseases, apart from inpatient or outpatient monitoring of patients, long term ECG monitoring is often required where the patients carry a portable ECG device. Furthermore, it is useful for heart patients to be able to perform an ECG reading, if needed, without the presence of medical professionals, for example in the case of so-called home monitoring. The risk of an untrained user interchanging the electrodes when attaching them to himself/herself—particularly when under stress—is significantly higher than with medical professionals. However, the untrained user would need a system that if needed or in an emergency, generate an ECG and reliably output the results, for example a warning that he/she should immediately get emergency medical care.

Another known way of avoiding permutations of the electrodes is a fixed arrangement of the electrodes by securing them to, for example, a vest, a belt, a harness or other mechanical means. However, such solutions are often inflexible because they cannot easily adapted to different body sizes or various anatomical circumstances. Furthermore, such systems are often uncomfortable to wear.

The objective of the present invention is to provide an improved device and an improved method for recording an electrocardiogram.

SUMMARY OF THE INVENTION

According to a first aspect the present invention provides a method for recording an electrocardiogram comprising the steps of: a) receiving electrocardiogram signals from at least two electrodes; b) calculating a current electrocardiogram from the received electrocardiogram signals, assuming an arrangement of the electrodes; c) determining a deviation of the calculated current electrocardiogram from a reference electrocardiogram; d) repeating the steps b) and c), wherein each repetition assumes a different electrode arrangement; and e) identifying which of the determined deviations is minimal.

According to another aspect the present invention provides an electrocardiogram device for recording an electrocardiogram comprising: two or more electrodes to output electrocardiogram signals; at least one storage means in which at least one reference electrocardiogram is saved; at least one processor unit equipped to perform a method according to the first aspect.

Further aspects and features of the present invention derive from the dependent claims, the attached drawings, and the following description of preferred exemplary embodiments.

SHORT DESCRIPTION OF THE DRAWINGS

Exemplary embodiments of the invention will now be described by way of example with reference to the attached drawing, where:

DESCRIPTION OF THE PREFERRED EXEMPLARY EMBODIMENTS

Figure 1:
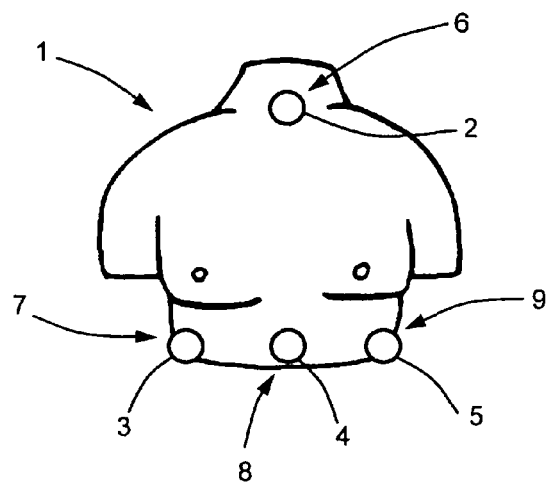
FIG. 1 illustrates a lead system with a first electrode arrangement.

FIG. 1 illustrates a lead system 1 with a first electrode arrangement of four electrodes 2, 3, 4, 5. Before a detailed description, some general explanations regarding the exemplary embodiments and their advantages are given below.

As described above, it occurs in the daily practice of using electrocardiographs that the electrodes are interchanged by a user, like a medical professional or a patient, while being attached. Particularly for an inexperienced user the arrangement of the electrodes is not always easily recognizable. Furthermore, inexperienced users will frequently be in a situation of stress when they attach the electrodes of an ECG device to themselves, for example at home, making it more difficult to recognize an incorrect electrode permutation. If the device then signals a "false alarm" due to the interchanged electrodes by, for example, indicating that the patient was suffering a heart attack, this might panic the user additionally—and entirely unnecessarily.

Furthermore, the inventor realized that the solution according to DE 100 65 578 A1, mentioned in the beginning, requires complex angle calculations in order to recognize incorrectly positioned electrodes. Moreover, this solution requires that the previously recorded reference result was obtained with a specified electrode arrangement, and interchanges are not allowed, even compared to the specifications. If the electrodes are interchanged during the recording of the reference result it will, with this solution, later not be possible to reliably recognize interchanged electrodes when recording a subsequent electrocardiogram.

The exemplary embodiments of the present invention recognize, for example, not only a "false" electrode permutation, but they are also able to recognize the kind of electrode permutation, and are capable to nevertheless output the "correct" electrocardiogram (ECG) from a reference electrocardiogram using, for example, a conversion. Therefore it is possible to determine a physiological change even when the electrodes are interchanged, for example when recording the current and/or the reference electrocardiogram, without having to record a new ECG. Furthermore, it is not necessary with the exemplary embodiments to know the arrangement of the electrodes when recording the reference electrocardiogram. Therefore it is possible to record the reference electrocardiogram and/or the current electrocardiogram with any unknown electrode permutation.

Electrocardiograms are created by recording electric signals via electrodes which are attached to a subject to be examined, in most cases in a specified position. In general a subject is a person. However, the present invention is not limited to humans but can, for example, also be used for animals.

The number of electrodes can vary depending on the lead system. Particularly lead systems using four, six, and ten electrodes are common. In order to measure a potential at least two electrodes are necessary because between two electrodes always just one potential difference can be measured. Accordingly, the electrocardiogram displays the course in time of potential differences between two individual electrodes.

The potential differences between the electrodes depend, among others, on the positioning of the electrodes on the subject to be examined because the electric currents in the heart muscle vary not only in time but also in location. Therefore it is possible to measure various activities in the heart muscle depending on the positioning of the electrodes and depending on the interpretation of the measured potential differences in time and location.

Hereafter some known ECG leads are explained by way of example, whereby the invention can be used for any lead system.

The potential differences created by the heart currents can be measured in various ways. These measurements are also called leads. It is known to differentiate them according to the measuring method, i.e. the kind of lead, and according to the position where the electrodes are attached Leads can, for example, be grouped into bipolar and unipolar leads according to the interconnection of the (lead) electrodes.

With a bipolar lead the electric voltage between two equivalent points on the body surface is registered, e.g. between the right arm and the left arm.

In contrast, the unipolar lead measures the voltage between a different electrode and an electrical "zero point", referred to as an indifferent electrode or reference electrode. To obtain the indifferent electrode two or more limb electrodes at a time are connected via resistors.

Moreover, the leads can be grouped according to the positions between which they are determined. A distinction is made, for example, between limb leads measuring the potential differences between the limbs, and the chest wall leads determined by the electrodes on the thorax.

For example, a conventional 12-channel ECG in parallel registers the limb leads according to their developers "Einthoven" and "Goldberger" as well as the chest wall lead according to "Wilson". Einthoven and Goldberger require three channels and Wilson six channels.

In addition, there are, for example, special leads according to "Nehb", "Frank" and "Dower".

The lead according to Nehb is considered to be an additional lead which is used for particular clinical questions. This is also the case for the lead according to Frank which is used as part of vectorcardiography.

The lead system described by Frank is based on vector considerations of an ECG with a momentary vector of the ECG being divided into the X, Y, and Z components of an orthogonal coordinate system. According to Frank linear equations are known which allow a transformation into the three leads X, Y, and Z from the potential differences of the electrodes. The three leads obtained in this way contain all information of the ECG and allow a vector illustration of the electric activity on different levels, for example with a two-dimensional display of two leads at a time as so-called "vector loops". Furthermore, equations are known which can be used to make the conventional 12-channel lead from the three orthogonal leads according to Frank.

With the lead system according to Dower it is possible to calculate the orthogonal leads X, Y, and Z across five electrodes (E, A, S, and I), including an additional ground electrode. Dower derives three leads from four electrodes, wherein one electrode is used as common reference pole. Analogous to the procedure of the Frank transformation it is also possible to calculate the conventional 12-channel ECG from the lead system according to Dower.

For some exemplary embodiments a lead according to Einthoven, Goldberger, Wilson, Nehb, Frank, or Dower is used to record the electrocardiogram. Depending on the exemplary embodiment an electrocardiogram device for recording an electrocardiogram accordingly comprises the number of electrodes necessary for the respective lead system (e.g. 2, 4, 5, 6, 8, or 10 electrodes), wherein any lead system can be used and any number of electrodes, depending on the used lead system.

The permutation or arrangement of the electrodes and the resulting deviation of a measured ECG from an earlier one is identified with a method for recording a electrocardiogram which runs, for example, in a control system of a electrocardiogram device, for example a electrocardiograph. For this purpose the electrocardiogram device comprises, for example, besides the control system, at least two electrodes for recording electrocardiogram signals and a storage means in which at least one reference electrocardiogram is saved. First at least two electrodes, for example attached to a person in a specified position, measure potential differences on the skin surface and send corresponding signals via signal lines, for example to a control system. Depending on the exemplary embodiment and the lead a varying number of electrodes are used, for example four, five, six or ten electrodes.

If several electrodes are used the control system measures the potential differences, usually always between the same electrodes which can however—as described above—be arranged differently in subsequent measurements due to incorrect positioning, or the signal lines may have been interchanged, for example when plugging them into the corresponding inputs of the electrocardiograph. The electrocardiograph or its control system does not recognize such an interchange but assumes for each measurement that the electrodes are arranged as specified.

The control system calculates a current electrocardiogram from the received electrocardiogram signals assuming an arrangement or permutation of the electrodes, for example as they are specified.

In the next step the control system determines a deviation of the calculated current electrocardiogram from a reference electrocardiogram, for example according to the Gaussian Error Model. The reference electrocardiogram has, for example, previously been saved in a memory by the control system and usually stems from the same subject as the current electrode signals. In some exemplary embodiments the reference electrocardiogram was recorded with a standard configuration while in others it was recorded with a non-standardized or permuted arrangement.

The determined deviation can be saved by the control system, for example in a memory. Then the control system assumes another electrode arrangement and calculates, based on this permutation, another current electrocardiogram based on the same electrocardiogram signals received. For this newly calculated second current electrocardiogram the control determines a (second) deviation from the reference electrocardiogram as well. This process is repeated by the control system until a current electrocardiogram is calculated and an associated deviation from the reference electrode arrangement is determined for each possible permutation of the electrode arrangement.

The number of permutations depends on the number of electrodes used. With two electrodes two arrangements are possible, with four electrodes it is factorial(4), i.e. 24 permutations. In general the number of permutations is determined by the function: factorial(number of electrodes).

After a part or—depending on the exemplary embodiment—all permutations have been calculated the control system identifies the minimal deviation. In addition it can identify and output the associated current electrocardiogram, and therefore ultimately also the arrangement of the electrodes for which the deviation between the reference electrocardiogram and the current electrocardiogram is minimal.

In some exemplary embodiments the control system outputs the electrocardiogram belonging to the minimal (smallest) deviation as current electrocardiogram. In some exemplary embodiments only the minimal deviation is produced as output or the minimal deviation together with the associated electrocardiogram. In other exemplary embodiments a derived signal is, for example, produced as output from the minimal deviation and/or the electrocardiogram.

By identifying the electrocardiogram with the minimal deviation, i.e. ultimately by (indirectly) identifying the actual electrode arrangement, the respective electrodes can be connected to any signal inputs of the control system. In other words, even if the electrodes are interchanged, for example during the current and/or the reference electrocardiogram, the "correct" electrocardiogram can nevertheless be outputted and a change of physiological parameters can be determined based on the "correct" identified ECG and/or based on the determined minimal deviation.

The output of the electrocardiogram is carried out in various ways. The electrocardiogram can, for example, be displayed on a display device like, for example, a screen or a plotter. On the other hand the electrocardiogram can also be outputted to memory, for example for the purpose of being saved there. The electrocardiogram for an assumed electrode arrangement is calculated by the control system, for example by adding the potentials received from the respective electrodes. In doing so the potentials of two electrodes can be added at any one time. However, in some exemplary embodiments more than two potentials are added. For example, it is possible to add the arithmetic average of two electrode potentials to the value of a third electrode.

In some exemplary embodiments, for example, the control system additionally determines from the minimal deviation and/or from the associated current electrocardiogram a change of a physiological parameter as, for example, blood flow, pumping function of the heart, cardiac arrhythmias and the like.

If, for example, the control system recognizes a change of a physiological parameter it outputs, in some exemplary embodiments, a warning signal and enables the patient to evaluate whether it is, for example, necessary to see a doctor or get emergency medical care. To facilitate the evaluation of his/her heart condition for the patient the control system outputs, for example, a numeric value depending on the amount of the deviation to represent the amount of the physiological change. In other exemplary embodiments the control system outputs the alarm signal, for example when the minimal deviation exceeds a predefined limit. In addition the control system can output various alarm signals for various limits. In this way the control system can give the alarm signal to the patient, for example in the form of a traffic light. At the first, low limit the patient sees a green light signal which tells him/her that no significant ECG change was measured. When the minimal deviation is above a second limit but below a third, the patient will be shown, for example, a yellow light which indicates that it is not necessary to get immediate medical attention but that he/she should soon seek treatment. A red signal will be displayed above the third limit and signals the patient that he/she should, for example, see a doctor immediately or even get emergency medical care. In some exemplary embodiments the control also directly outputs the deviation. In some exemplary embodiments the control also outputs the identified electrode arrangement with the minimal deviation.

Referring to FIG. 1, it shows how a first arrangement of four electrodes 2, 3, 4, 5 is attached to a patient at the respective positions 6, 7, 8, 9 in order to measure a reference ECG. In this first arrangement electrode 2 is placed at position 6, electrode 3 at position 7, electrode 4 at position 8 and electrode 5 at position 9.

Figure 2:
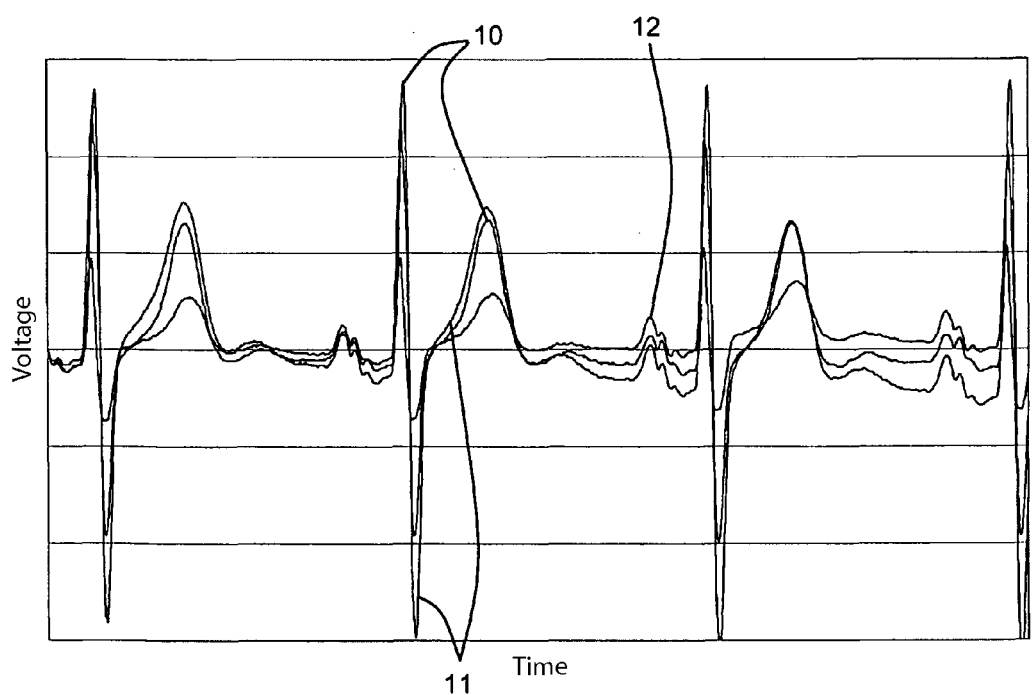
FIG. 2 shows the potential curve as reference ECG measured with the electrode arrangements according to FIG. 1.

Measuring the electrode signals arranged in the first arrangement according to FIG. 1 generates, for example, the ECG as shown in FIG. 2. This ECG is generated by measuring the course in time of the potential differences between the zero-position, i.e. position 6 and one of the remaining three positions 7, 8 and 9 respectively:

$$V(\text{electrode } 3,t) - V(\text{electrode } 2,t) = V_1(\text{position 7, position 6}, t);$$

$$V(\text{electrode } 4,t) - V(\text{electrode } 2,t) = V_2(\text{position 8, position 6}, t); \text{ and}$$

$$V(\text{electrode } 5,t) - V(\text{electrode } 2,t) = V_3(\text{position 9, position 6}, t);$$

wherein "V" is the correspondingly measured potential voltage and "t" is the time variable. The course in time of each measured potential difference $V_1$, $V_2$, $V_3$ is illustrated in FIG. 2 by the curves 10, 11 and 12, i.e., $V_1$ corresponds to the dark curve 10, $V_2$ corresponds to the medium gray curve 11 and $V_3$ corresponds to the light colored curve 12.

Figure 3:
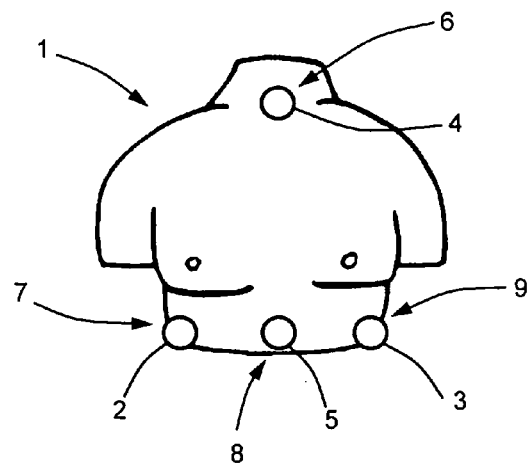
FIG. 3 illustrates the lead system according to FIG. 1 with a second electrode arrangement.
Figure 4:
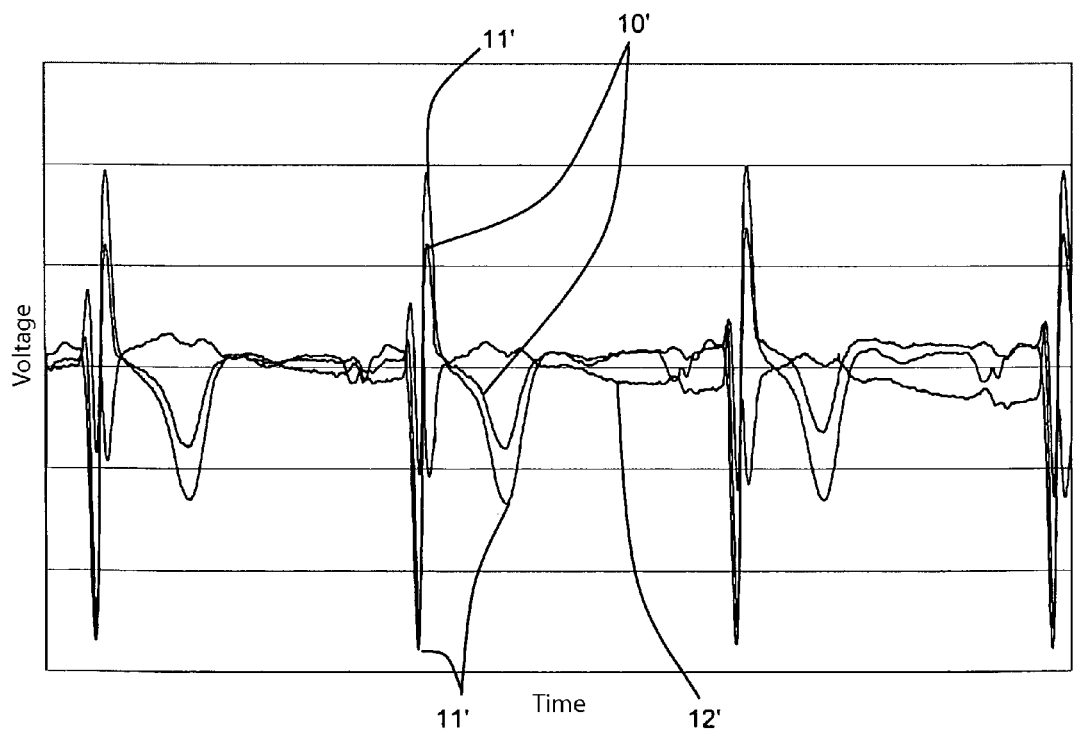
FIG. 4 shows the potential curve measured with the electrode arrangement according to FIG. 3.

A permutation of the electrodes, for example electrode 4 to position 6, electrode 2 to position 7, electrode 5 to position 8 and electrode 3 to position 9, as shown in FIG. 3, leads to a different ECG than the one shown in FIG. 4. It is different from the reference ECG according to FIG. 2 when the potentials between the same electrodes are measured in the same way as in the reference ECG, as an electrocardiograph will do because it doesn't "know" that the electrodes have been interchanged:

$$V(\text{electrode } 3,t) - V(\text{electrode } 2,t) = V_1(\text{position 9, position 7}, t);$$

$$V(\text{electrode } 4,t) - V(\text{electrode } 2,t) = V_2(\text{position 6, position 7}, t); \text{ and}$$

$$V(\text{electrode } 5,t) - V(\text{electrode } 2,t) = V_3(\text{position 8, position 7}, t);$$

Because the electrocardiograph always measures the potential differences between the same electrode/signal inputs, it results from the equations that the potentials are determined between other positions than in the reference ECG. Therefore the resulting curves 10', 11' and 12' for the potentials $V_1$, $V_2$ and $V_3$ are different than the respective curves 10, 11 and 12 of the reference ECG according to FIG. 2. By using an appropriate conversion or by permutation of the electrode arrangement, the potentials between the positions, as they were used for the reference ECG according to FIG. 2, can be determined or calculated respectively:

$$V_1(\text{position 7, position 6}, t) = -(V(\text{electrode 4}, t) - V(\text{electrode 2}, t));$$

$$V_2(\text{position 8, position 6}, t) =$$
$$-(V(\text{electrode 4}, t) - V(\text{electrode 2}, t)) + +V(\text{electrode 5}, t) -$$
$$V(\text{electrode 2}, t);$$

$$V_3(\text{position 9, position 6}, t) =$$
$$-(V(\text{electrode 4}, t) - V(\text{electrode 2}, t)) + +V(\text{electrode 3}, t) -$$
$$V(\text{electrode 2}, t);$$

Figure 5:
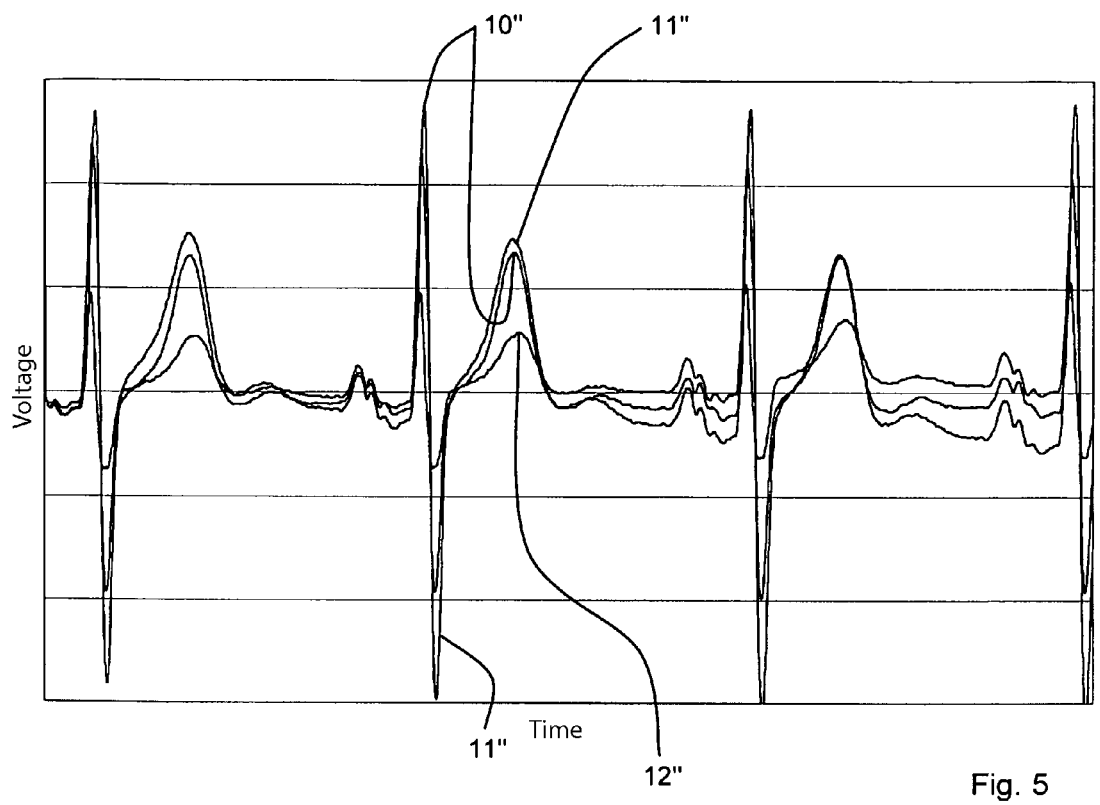
FIG. 5 illustrates a comparison of the potential curve of FIG. 4 with the reference ECG of FIG. 2.

This conversion results in the ECG according to FIG. 5 where $V_1$ is equivalent to curve 10'', $V_2$ is equivalent to curve 11'' and $V_3$ is equivalent to curve 12''. This converted ECG essentially corresponds to the reference ECG according to FIG. 2, as can be easily seen when comparing the two ECGs from FIG. 2 and FIG. 5, because the actual electrode arrangement was assumed for the calculation. In other words, this conversion mathematically maps the interchanged electrode arrangement and the associated potential curves on the "correct" one of the reference ECG.

This conversion is ultimately equivalent to a vector addition. For example, adding the vector between position 6 and 7 in FIG. 1 to the vector between position 7 and 8 results in vector $V_2$ which lies between position 6 and 7. Analogously, adding the vectors between position 6, 7 and 7, 9 results in vector $V_3$ which lies between position 9 and 6. This vector addition is based on the assumption that the sum of the potentials in a vector triangle, e.g. between position 6, 7, 8 or 6, 7, 9, is constant.

Figure 6:
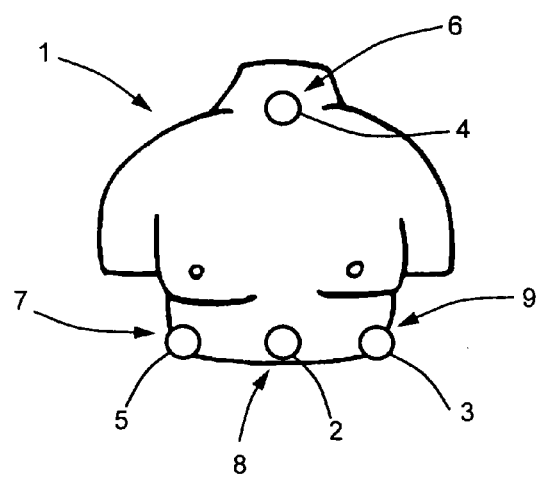
FIG. 6 illustrates the lead system according to FIG. 1 with a third electrode arrangement.

Another permutation of the electrode arrangement is shown in FIG. 6 where electrode 4 is placed at position 6, electrode 5 at position 7, electrode 2 at position 8 and electrode 3 at position 9. For the potential calculation this results in the following if, again, it is assumed that the electrodes are actually in the positions according to FIG. 1 as the electrocardiograph will assume:

$$V(\text{electrode } 3,t) - V(\text{electrode } 2,t) = V_1(\text{position 9, position 8}, t);$$

$$V(\text{electrode } 4,t) - V(\text{electrode } 2,t) = V_2(\text{position 6, position 8}, t); \text{ and}$$

$$V(\text{electrode } 5,t) - V(\text{electrode } 2,t) = V_3(\text{position 7, position 8}, t);$$

Figure 7:
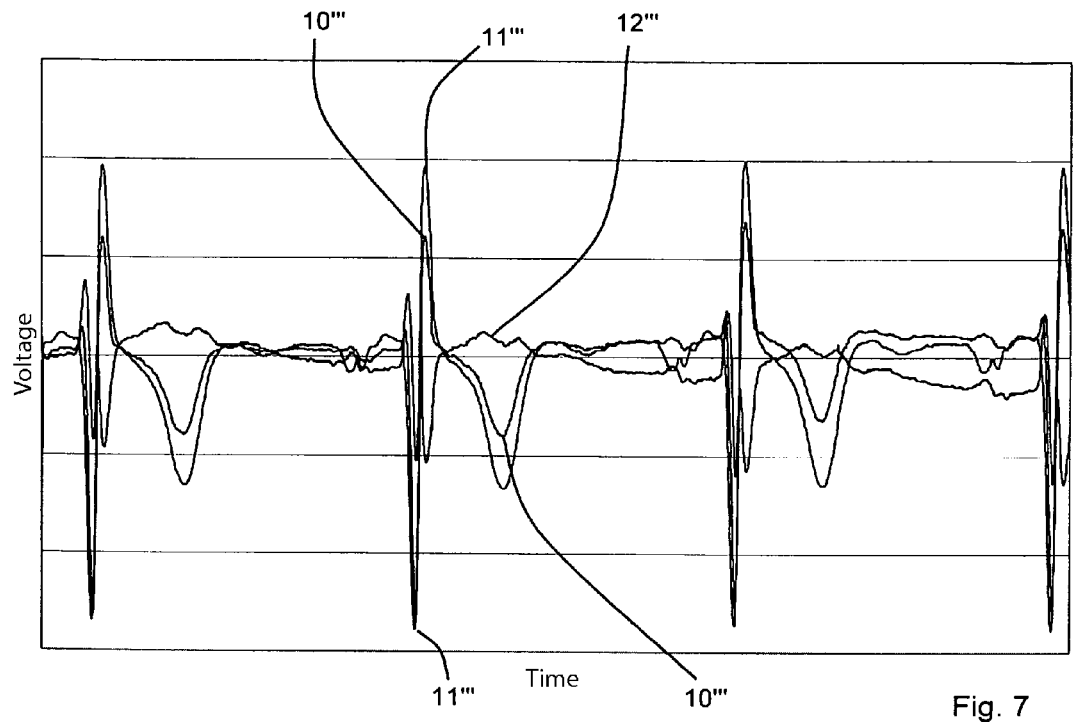
FIG. 7 shows the potential curve measured with the electrode arrangement according to FIG. 6.

The resulting ECG shows FIG. 7 with curve 10''' illustrating the potential curve $V_1$, curve 11''' illustrating the potential curve $V_2$, and curve 12''' illustrating the potential curve $V_3$.

If the same electrode arrangement is assumed in this case as explained in connection with FIG. 5, the following ECG is obtained:

$$V_1(\text{position 7, position 6}, t) = -(V(\text{electrode 4}, t) - V(\text{electrode 2}, t));$$

$$V_2(\text{position 8, position 6}, t) =$$
$$-(V(\text{electrode 4}, t) - V(\text{electrode 2}, t)) + +V(\text{electrode 5}, t) -$$
$$V(\text{electrode 2}, t);$$

$$V_3(\text{position 9, position 6}, t) =$$
$$-(V(\text{electrode 4}, t) - V(\text{electrode 2}, t)) + +V(\text{electrode 3}, t) -$$
$$V(\text{electrode 2}, t);$$

Figure 8:
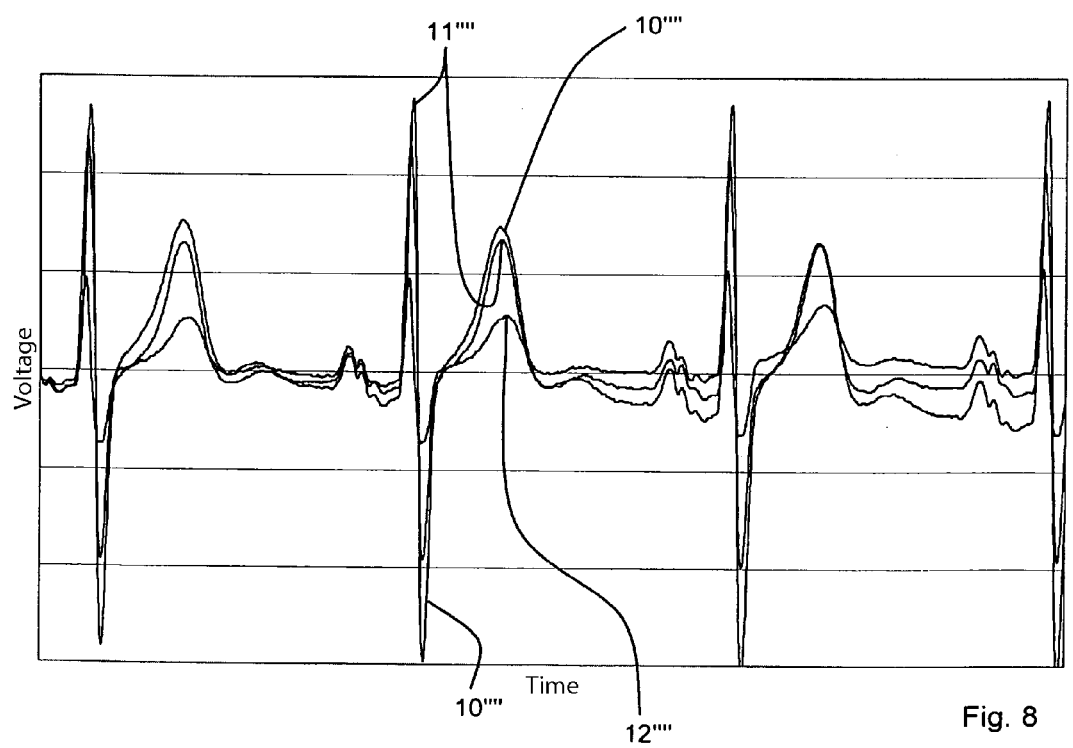
FIG. 8 illustrates a comparison of the potential curve of FIG. 7 with the reference ECG of FIG. 2.

The ECG resulting from this calculation is illustrated in FIG. 8 and the curves 10'''', 11'''', 12'''' show the potential curves $V_1$, $V_2$ and $V_3$ respectively. As can easily be seen when comparing the ECG from FIG. 8 with the reference ECG according to FIG. 2. the curves 10'''' and 11'''' are interchanged compared to the reference ECG. The assumed electrode arrangement was therefore not correct—which is not surprising because the calculation above of the ECG according to FIG. 8 is based on the assumed permutation of FIG. 3 which is obviously different from that of FIG. 6.

Figure 9:
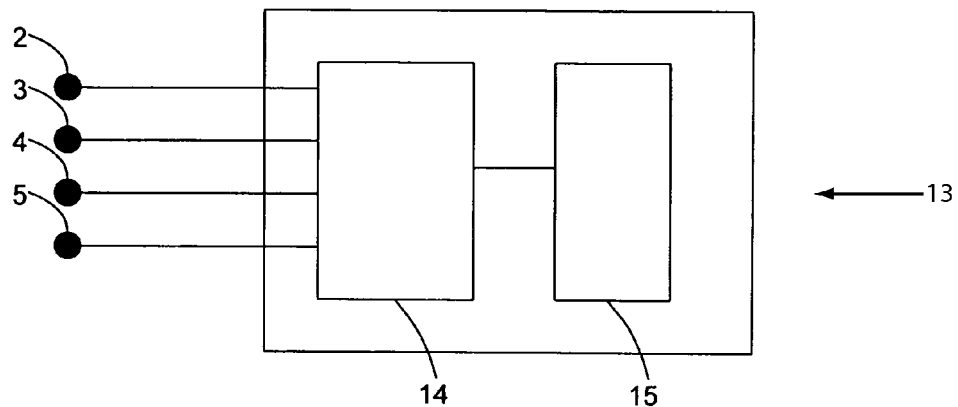
FIG. 9 shows an exemplary embodiment of an electrocardiogram device according to the present invention and FIG. 10 shows an exemplary embodiment of a method for recording an electrocardiogram according to the present invention.
Figure 10:
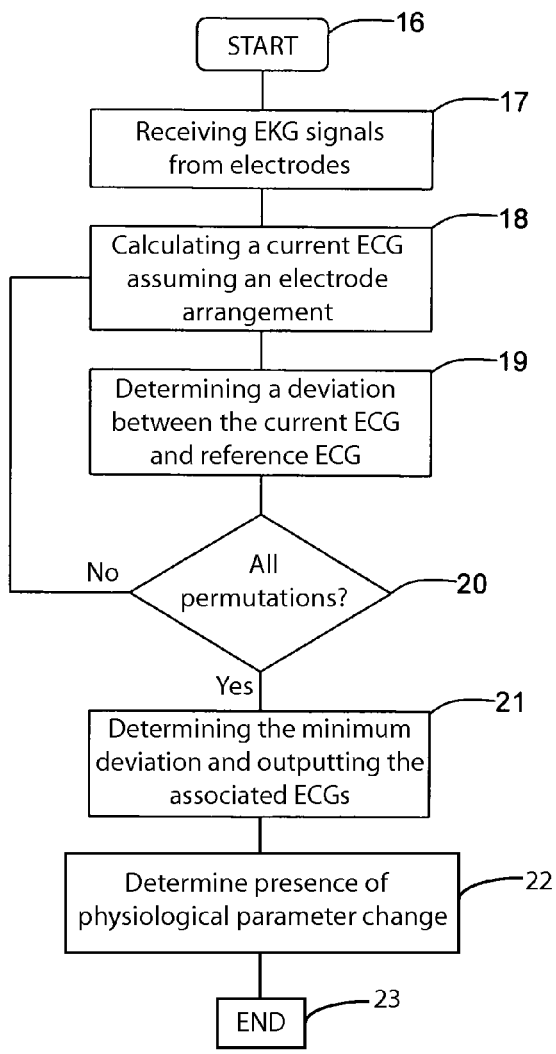

The electrocardiograms shown before can, for example, be recorded with a mobile ECG device 13 as illustrated schematically in FIG. 9. Besides the electrodes 2, 3, 4, 5 the mobile ECG comprises a control system 14 and a memory 15. The ECG device or the control system of the ECG device respectively, is designed to perform the method according to FIG. 10 which starts at 16 and ends at 22.

For this purpose the control system 14, in a first step 17, receives and analyzes corresponding electrode signals from electrodes 2, 3, 4, 5 attached to a patient. Thus the ECG device 13 first receives ECG signals from electrodes 2, 3, 4, 5 in an arrangement as illustrated in FIG. 1. The control system calculates the corresponding potential curves 10, 11, 12 from these electrode signals as illustrated in FIG. 2. This resulting ECG is then saved in the memory 14 by the ECG device 13 as reference ECG for later comparison. When the patient reattaches the electrodes 2, 3, 4, 5 to himself/herself at a later time the control system calculates a (first) current ECG from the now currently received ECG signals in a step 18, whereby the control 14 assumes a first electrode arrangement—for example the arrangement of the reference ECG. It is possible that the patient has interchanged the electrodes compared to the arrangement associated to the reference ECG. Or the patient has, for example, interchanged the signal lines of the electrodes when plugging them into the ECG device.

In this case the control system 14 assumes the electrode arrangement used for recording the reference ECG when calculating the current ECG. However, it is not necessary for the control system 14 to know the electrode arrangement of the reference ECG because the control system subsequently assumes all possible electrode arrangements and calculates the minimal deviation, and is therefore able to identify the electrocardiogram corresponding to the reference ECG even if the arrangement for the reference ECG is not known. The calculation of the current ECG with the correspondingly assumed electrode arrangement is then performed, for example, analogous to the one described above by corresponding permutation of the electrodes and potential addition.

In a next step 19 the control system 14 determines a deviation between the currently calculated ECG which is based on the assumed electrode arrangement and the reference ECG which is saved in the memory 15. The permutation of electrodes 2, 3, 4, 5 can be, for example, as illustrated in FIG. 3 or FIG. 6.

In a step 20 the control system 14 checks whether it has already run all possible permutations, i.e. electrode arrangements, and compared them with the reference ECG. If this is not the case the control system 14 jumps back to step 18 and checks current electrocardiograms based on assumed electrode arrangements until condition 20 is fulfilled. The thus determined deviations between the currently determined ECG, assuming a corresponding electrode arrangement, are stored by the control system 14 in the memory 15 as well. After the control system 14 has calculated and compared all permutations and determined the associated deviations, it determines the minimal deviation of the determined deviations in step 21 and outputs, for example, the ECG associated to the minimum deviation or the minimum deviation itself or a signal derived from it, for example a display (not shown) on the ECG device 13. In step 22, the presence of a change of a physiological parameter is determined when the determined minimal deviation is greater than or equal to a predefined limit.

From the determined minimal deviation the control system can conclude a change of a physiological parameter. Such a parameter can concern, for example, the pumping performance, the blood flow in the heart or an arrhythmia. Depending on the settings the control system can output the deviation, for example in the form of a numeric value or in the form of a colored display.

In some exemplary embodiments the ECG device 13 comprises three light-emitting diodes, one green, one yellow and one red. The control system compares the determined minimal deviation with predefined limits which are associated with the corresponding colors of the LED. Thus the ECG device 13 is able to signal the patient's condition similar to a stop light. For example, green signals that no significant ECG changes can be measured which would indicate a possibly aggravated medical condition; yellow signals that a doctor visit in the near future is indicated and red signals that there is acute danger. The control system 14 operates, for example, such that the green LED is lit in case of a minimal deviation below a first predefined limit. If the minimal deviation is between the first and a second predefined limit, the yellow LED will be lit. If the minimal deviation is above the second limit, the yellow LED will be lit.

Determining the minimal deviation is used in some exemplary embodiments to identify the actual electrode arrangement and, therefore, the ECG associated with the minimal deviation. Then the control system can, in some exemplary embodiments, perform another analysis and, for example, a detailed comparison between the current ECG and the reference ECG, and therefore perform specific deviations, for example between corresponding potential curves (e.g. between 10 and 10", 11 and 11", 12 and 12") and sections thereof. In some exemplary embodiments further output of a specific alarm signal is, for example, then based on such a specific analysis. For example, the ECG device can output a specific alarm signal depending on physiological parameters.

The invention claimed is:

1. A method for recording an electrocardiogram, comprising the steps of:
    a) receiving electrocardiogram signals from at least two electrodes and recording the received signals in a memory;
    b) calculating a current electrocardiogram from the received electrocardiogram signals, assuming a proper arrangement of the electrodes;
    c) determining a deviation of the calculated current electrocardiogram from a reference electrocardiogram;
    d) repeating steps b) and c) using different electrode arrangements to determine deviations for each arrangement;
    e) determining an arrangement with a minimal deviation;
    f) determining from the arrangement with the minimal deviation a change of a physiological parameter; and
    g) activating an alarm signal when the minimal deviation exceeds a predefined limit,
    wherein the physiological parameter is pumping performance, blood flow, or arrhythmia of a user's heart.

2. A method according to claim 1, wherein, in addition, the current electrocardiogram with the minimal deviation is outputted.

3. A method according to claim 1, wherein the reference electrocardiogram is recorded from a same subject as the received electrocardiogram signals.

4. A method according to claim 1, wherein the current electrocardiogram is based on addition of respective potentials of the electrode signals.

5. A method according to claim 1, wherein the steps c) and d) are repeated until each possible electrode arrangement has been assumed at least once.

6. A method according to claim 1, wherein electrode signals are received with a lead according to Einthoven, Goldberger, Wilson, Nehb, Frank, or Dower.

7. A method according to claim 6, wherein a numeric value, representing an amount of the physiological change, is outputted depending on an amount of a deviation.

8. A method according to claim 1, wherein the minimal deviation is outputted.

9. A method according to claim 1, wherein an identified electrode arrangement is outputted.

10. An electrocardiogram device for recording an electrocardiogram, comprising:

at least two electrodes for recording electrocardiogram signals;

at least one storage means where at least one reference electrocardiogram is saved; and at least one control system equipped to perform a method according to claim 1.

11. An electrocardiogram device according to claim 10 comprising a lead system according to Einthoven, Goldberger, Wilson, Nehb, Frank or Dower.

12. An electrocardiogram device according to claim 11, wherein the electrocardiogram device is equipped to output different alarm signals for different limits.

13. An electrocardiogram device according to claim 10, wherein the electrocardiogram device is equipped to output an alarm signal when the minimal deviation exceeds a predefined limit.

14. An electrocardiogram device according to claim 13, wherein the electrocardiogram device is equipped to output different alarm signals for different limits.

15. An electrocardiogram device according to claim 10, wherein the electrocardiogram device is equipped to output different alarm signals for different limits.

\* \* \* \* \*